US012637717B2

(12) United States Patent
Liao et al.

(10) Patent No.: US 12,637,717 B2
(45) Date of Patent: May 26, 2026

(54) METHOD FOR TREATING AND PREDICTING PROGNOSIS OF GASTRIC CANCER PATIENT BY CALCULATING RNA EXPRESSION WITH LOGISTIC REGRESSION

(71) Applicant: National Yang Ming Chiao Tung University, Hsinchu City (TW)

(72) Inventors: Kuang-Wen Liao, Hsinchu City (TW); Cheng-Hsun Chuang, Tainan City (TW)

(73) Assignee: National Yang Ming Chiao Tung University, Hsinchu City (TW)

( * ) Notice: Subject to any disclaimer, the term of this patent is extended or adjusted under 35 U.S.C. 154(b) by 877 days.

(21) Appl. No.: 17/880,809

(22) Filed: Aug. 4, 2022

(65) Prior Publication Data

US 2023/0332240 A1      Oct. 19, 2023

(30) Foreign Application Priority Data

Apr. 15, 2022    (TW) .................................. 111114564

(51) Int. Cl.
*C12Q 1/6886*        (2018.01)
(52) U.S. Cl.
CPC ...... *C12Q 1/6886* (2013.01); *C12Q 2600/112* (2013.01); *C12Q 2600/118* (2013.01); *C12Q 2600/158* (2013.01)
(58) Field of Classification Search
None
See application file for complete search history.

(56) References Cited

U.S. PATENT DOCUMENTS

| | | |
|---|---|---|
| 2007/0048749 A1 | 3/2007 | Chen et al. |
| 2019/0241972 A1 | 8/2019 | Huh |

FOREIGN PATENT DOCUMENTS

| | | |
|---|---|---|
| TW | I359198 B | 3/2012 |

OTHER PUBLICATIONS

Hao, Shuhong, et al. "Identification of key genes and circular RNAs in human gastric cancer." Medical science monitor: international medical journal of experimental and clinical research 25 (2019): 2488.*
Cho, Jae Yong, et al. "Gene expression signature-based prognostic risk score in gastric cancer." Clinical cancer research 17.7 (2011): 1850-1857.*
Huang, Lei, Ruo-Lin Wu, and A-Man Xu. "Epithelial-mesenchymal transition in gastric cancer." American journal of translational research 7.11 (2015): 2141.*
"Comprehensive molecular characterization of gastric adenocarcinoma," The Cancer Genome Atlas Research Network, Nature, 2014, pp. 202-209, vol. 513.
Cristescu et al., "Molecular analysis of gastric cancer identifies subtypes associated with distinct clinical outcomes," Nature Medicine, 2015, pp. 449-456, vol. 21:5.
Oh et al., "Clinical and genomic landscape of gastric cancer with a mesenchymal phenotype," Nature Communications, 2018, pp. 1-14, vol. 9:1777.
Bauer et al., "A novel pretherapeutic gene expression-based risk score for treatment guidance in gastric cancer", Annals of Oncology, 2018, pp. 127-132, vol. 29.
Li et al., "A Novel Six-Gene-Based Prognostic Model Predicts Survival and Clinical Risk Score for Gastric Cancer", Frontiers in Genetics, 2021, pp. 1-15, vol. 12, Article 615834.
Wang et al., "Identification of potential key genes in gastric cancer using bioinformatics analysis", Biomedical Reports, 2020, pp. 178-192, vol. 12.

* cited by examiner

*Primary Examiner* — G. Steven Vanni
(74) *Attorney, Agent, or Firm* — The Webb Law Firm

(57)        ABSTRACT

A method for predicting a prognosis of a gastric cancer patient is provided, including measuring expression levels of five RNAs in a sample of the gastric cancer patient, and the five RNAs being ANTXR1, COL6A3, THBS2, THBS4, and SFRP4; and comparing the expression levels of the five RNAs in the sample with expression levels of the five RNAs in a control, in which the gastric cancer patient is identified as having a poor prognosis when the expression levels of the five RNAs in the sample are lower than the expression levels of the five RNAs in the control.

16 Claims, 16 Drawing Sheets

METHOD FOR TREATING AND PREDICTING PROGNOSIS OF GASTRIC CANCER PATIENT BY CALCULATING RNA EXPRESSION WITH LOGISTIC REGRESSION

CROSS-REFERENCE TO RELATED APPLICATION

This application claims priority to Taiwanese Application Number 111114564 filed Apr. 15, 2022, the disclosure of which is hereby incorporated by in its entirety.

BACKGROUND OF THE INVENTION

Field of Invention

The present disclosure relates to a prediction method and a kit thereof, and more particularly, to a method for predicting a prognosis of a gastric cancer patient and a kit therefor.

Description of Related Art

It is difficult to detect early gastric cancer, and about 50% of patients have metastasized at initial diagnoses, resulting in worse prognoses than other cancers. Current studies have also found that about 20% of gastric cancer patients belong to molecular subtypes that are easier to metastasize and have characteristics of easy relapse.

Currently, no technology that can perform multi-parameter evaluation and screening based on biological characteristics of ideal tumor targets or tumor-associated antigens can identify biomarkers that are overexpressed in specific cancer subgroups. In addition, current related technologies only classify gastric cancer based on molecular-level information to explore whether there are significant differences in prognoses of different subtypes. Most of them do not further design models for subtypes with poor prognoses to predict their prognoses, or do not provide better prediction rates and are not validated by multiple independent datasets.

Therefore, in order to identify biomarkers representing different gastric cancer subtypes, the existing technology needs to be improved.

SUMMARY OF THE INVENTION

A purpose of one embodiment of the present disclosure is to provide a method and a kit for predicting a prognosis or recurrence of a gastric cancer patient, so as to identify different gastric cancer subtypes and improve a prognosis prediction rate and a survival probability.

One embodiment of the present disclosure provides a method for predicting a prognosis of a gastric cancer patient, which includes: measuring expression levels of five ribonucleic acids (RNAs) in a sample of the gastric cancer patient, the five RNAs being ANTXR1, COL6A3, THBS2, THBS4 and SFRP4; and calculating the five RNAs by a logistic regression model to obtain a risk ratio, in which when the risk ratio is greater than 0.5, the gastric cancer patient is identified as mesenchymal phenotype of a gastric cancer subtype, and the prognosis is poor.

One embodiment of the present disclosure provides a method for predicting a prognosis of a gastric cancer patient and treating the gastric cancer patient, which includes: measuring expression levels of five ribonucleic acids (RNAs) in a sample of the gastric cancer patient, the five RNAs being ANTXR1, COL6A3, THBS2, THBS4 and SFRP4; calculating the five RNAs by a logistic regression model to obtain a risk ratio, in which when the risk ratio is greater than 0.5, the gastric cancer patient is identified as mesenchymal phenotype of a gastric cancer subtype, and the prognosis is poor; and administrating a treatment to the human who is at risk of mesenchymal phenotype of the gastric cancer subtype with a suitable therapy, in which the treatment is a gastric resection surgery, chemotherapy, radiation therapy, or a combination thereof.

In some embodiments, the sample is ex vivo gastric tissue.

In some embodiments, a detection method of the expression levels of the five RNAs includes microarray, polymerase chain reaction, or sequencing.

In some embodiments, the polymerase chain reaction includes real-time polymerase chain reaction or digital polymerase chain reaction.

In some embodiments, the sequencing includes next-generation sequencing, single-molecule real-time sequencing, or nanopore sequencing.

In some embodiments, calculating the five RNAs by the logistic regression model includes: calculating the five RNAs by the logistic regression model to obtain a risk value $Y1=3.9208*(ANTXR1)-0.7496*(SFRP4)+0.8110*(THBS2)+2.6519*(THBS4)+0.9169*(COL6A3)-23.0876$ Equation (1); and transforming the risk value Y1 through a sigmoid function to obtain the risk ratio between 0 and 1.

In some embodiments, calculating the five RNAs by the logistic regression model includes: calculating the five RNAs by the logistic regression model to obtain a risk value $Y2=2.9090*(ANTXR1)-0.5372*(SFRP4)-0.7406*(THBS2)+2.4313*(THBS4)+2.6100*(COL6A3)-24.1446$ Equation (2); and transforming the risk value Y2 through a sigmoid function to obtain the risk ratio between 0 and 1.

Another embodiment of the present disclosure provides a method for predicting a prognosis of a gastric cancer patient, which includes: measuring expression levels of five RNAs in a sample of the gastric cancer patient, and the five RNAs being ANTXR1, COL6A3, THBS2, THBS4 and SFRP4; calculating the expression levels of the five RNAs in the sample of the gastric cancer patient by a receiver operating characteristic curve to obtain an area under curve of the gastric cancer patient; calculating the five RNAs by a logistic regression model to obtain a risk ratio; and evaluating a risk of a poor prognosis of the gastric cancer patient, in which when the risk ratio is greater than 0.5, the gastric cancer patient is identified as mesenchymal phenotype of a gastric cancer subtype, and the prognosis is poor.

Another embodiment of the present disclosure provides a method for predicting a prognosis of a gastric cancer patient and treating the gastric cancer patient, which includes: measuring expression levels of five RNAs in a sample of the gastric cancer patient, and the five RNAs being ANTXR1, COL6A3, THBS2, THBS4 and SFRP4; calculating the expression levels of the five RNAs in the sample of the gastric cancer patient by a receiver operating characteristic curve to obtain an area under curve of the gastric cancer patient; calculating the five RNAs by a logistic regression model to obtain a risk ratio; evaluating a risk of a poor prognosis of the gastric cancer patient, in which when the risk ratio is greater than 0.5, the gastric cancer patient is identified as mesenchymal phenotype of a gastric cancer subtype, and the prognosis is poor; and administrating a treatment to the human who is at risk of mesenchymal phenotype of the gastric cancer subtype with a suitable therapy, wherein the treatment is a gastric resection surgery, chemotherapy, radiation therapy, or a combination thereof.

In some embodiments, the area under curve of the gastric cancer patient is greater than 0.9.

In some embodiments, the sample is ex vivo gastric tissue.

In some embodiments, a detection method of the expression levels of the five RNAs includes microarray, polymerase chain reaction, or sequencing.

In some embodiments, the polymerase chain reaction includes real-time polymerase chain reaction or digital polymerase chain reaction.

In some embodiments, the sequencing includes next-generation sequencing, single-molecule real-time sequencing, or nanopore sequencing.

Another embodiment of the present disclosure provides a kit for predicting a prognosis of a gastric cancer patient, which includes: five reagents configured to identify expression levels of five RNAs in a sample of the gastric cancer patient, and the five RNAs being ANTXR1, COL6A3, THBS2, THBS4 and SFRP4.

In some embodiments, the five reagents include primer pairs, probes, or a combination thereof.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion. The disclosure can be more fully understood by reading the following detailed description of the embodiment, with reference made to the accompanying drawings as follows.

4

Figure 11:
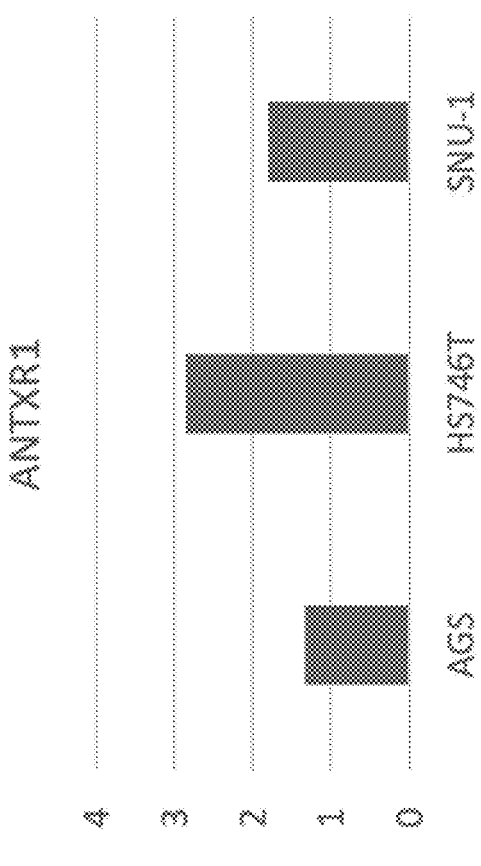
Figure 11:
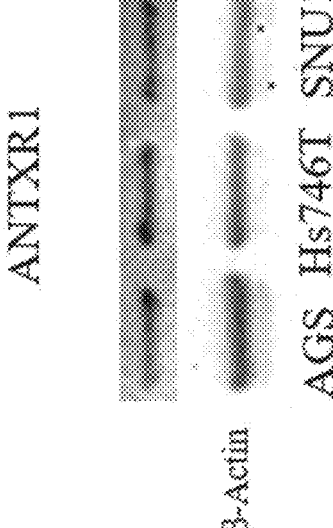

FIG. 11 shows an ANTXR1 protein electrophoresis and its quantification according to one embodiment of the present disclosure; β-actin is a housekeeping gene as an internal control.

Figure 12:
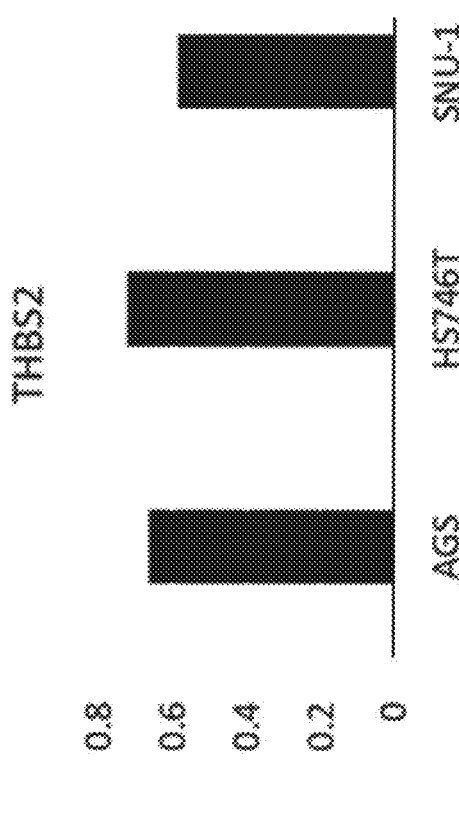
Figure 12:
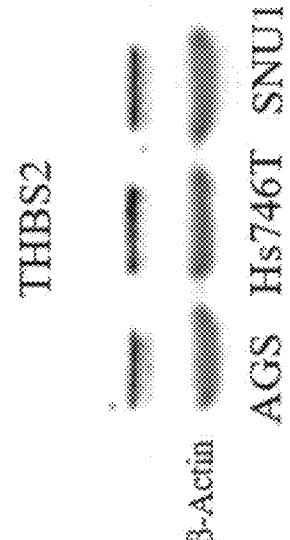

FIG. 12 shows a THBS2 protein electrophoresis and its quantification according to one embodiment of the present disclosure; β-actin is a housekeeping gene as an internal control.

Figure 13:
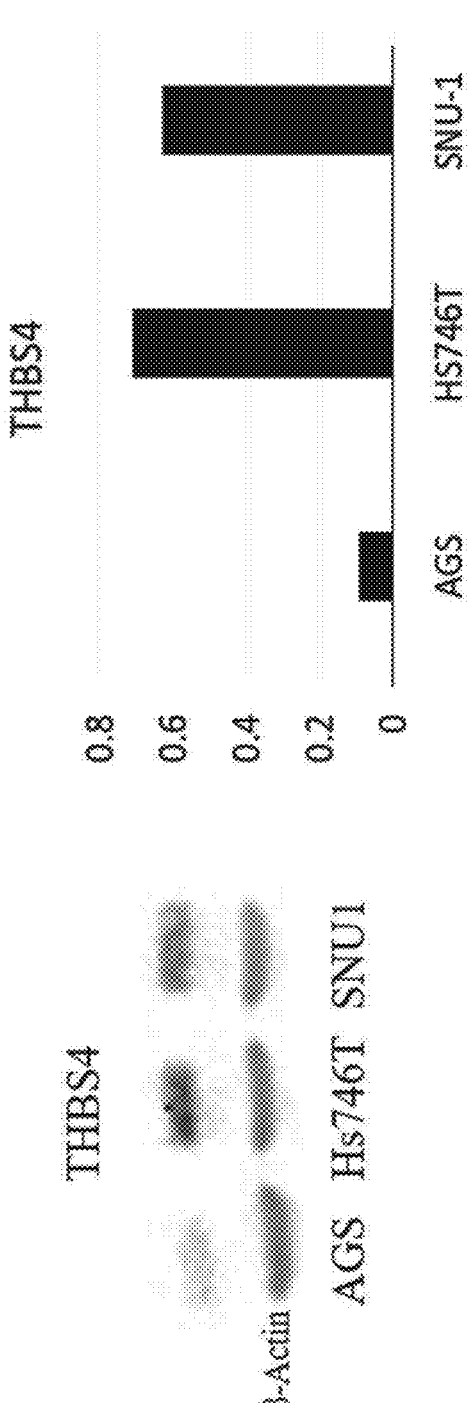

FIG. 13 shows a THBS4 protein electrophoresis and its quantification according to one embodiment of the present disclosure; β-actin is a housekeeping gene as an internal control.

Figure 14:
Figure 14:
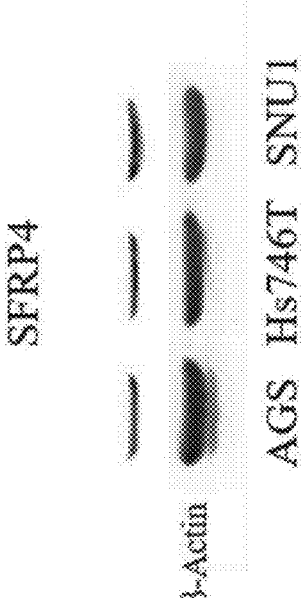

FIG. 14 shows a SFRP4 protein electrophoresis and its quantification according to one embodiment of the present disclosure; β-actin is a housekeeping gene as an internal control.

Figure 15:
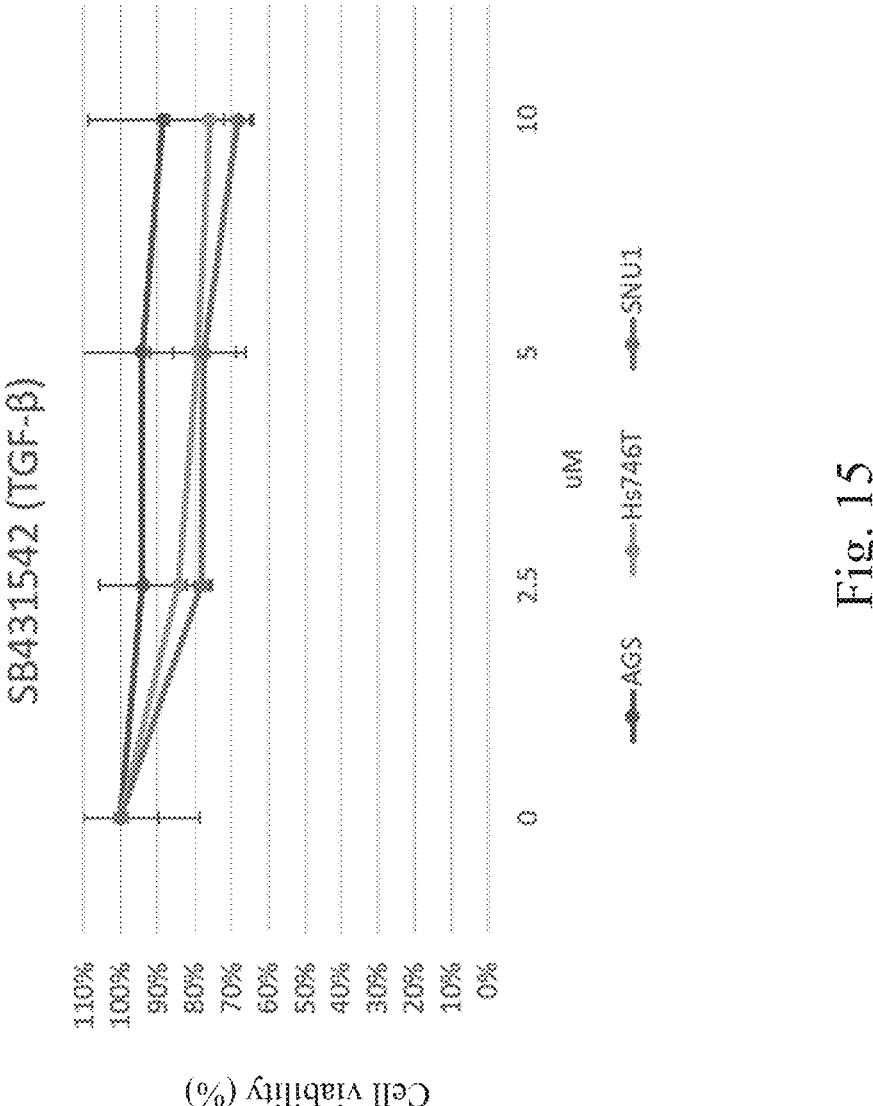

FIG. 15 is a line chart of cell viability after treatment with a TGF-β inhibitor according to one embodiment of the present disclosure.

Figure 16:
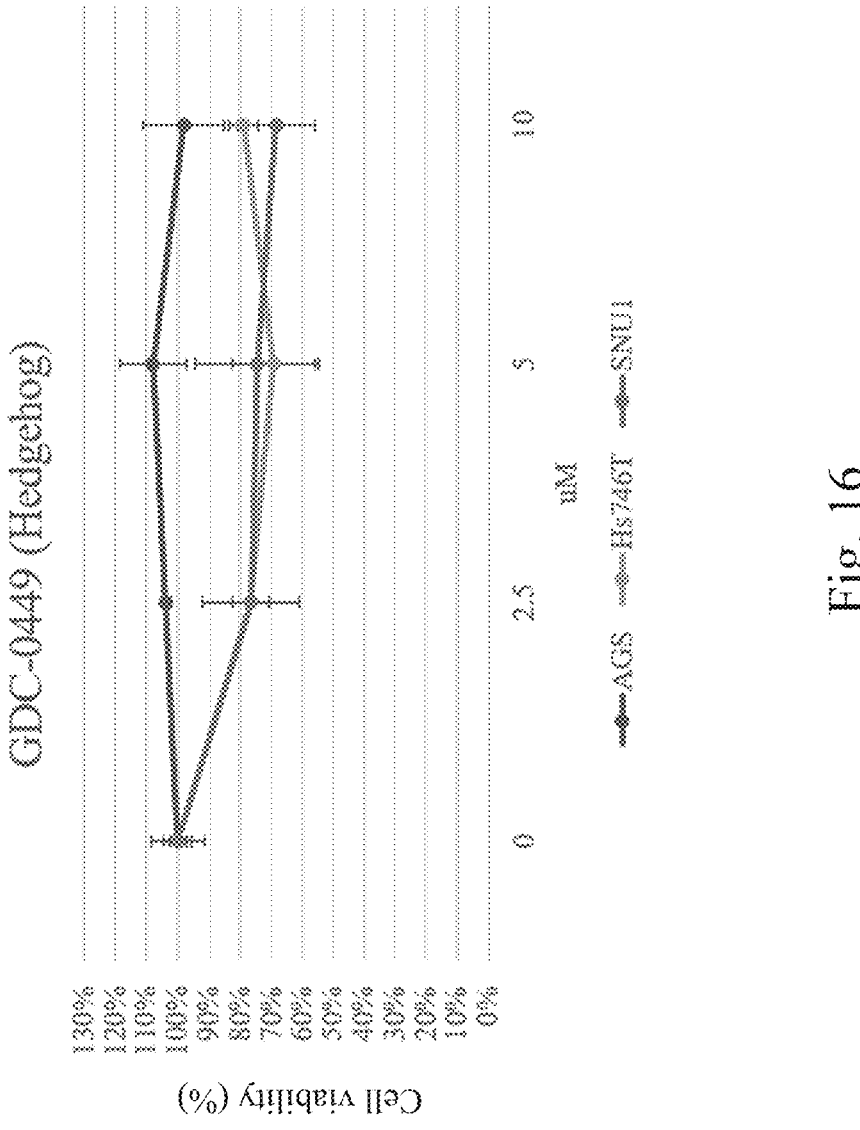

FIG. 16 is a line chart of cell viability after treatment with a hedgehog inhibitor according to one embodiment of the present disclosure.

DESCRIPTION OF THE INVENTION

The following disclosure provides detailed description of many different embodiments, or examples, for implementing different features of the provided subject matter. These are, of course, merely examples and are not intended to limit the disclosure but to illustrate it. In addition, various embodiments disclosed below may combine or substitute one embodiment with another, and may have additional embodiments in addition to those described below in a beneficial way without further description or explanation. In the following description, many specific details are set forth to provide a more thorough understanding of the present disclosure. It will be apparent, however, to those skilled in the art, that the present disclosure may be practiced without these specific details.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", or "includes" and/or "including", or "has" and/or "having" when used in this specification, specify the presence of stated features, regions, integers, steps, operations, elements, and/or components, but do not preclude the presence or addition of one or more other features, regions, integers, steps, operations, elements, components, and/or groups thereof.

The present disclosure relates to a method for judging a cancer subtype and a prognosis of a gastric cancer patient, which relates to measurements of expression levels of five RNAs from an individual biological sample, and the measured expression levels are used to predict risks of metastasis, survival and recurrence for a carcinoma in situ sample. The expression levels of the specific RNAs in this method are used to calculate a recurrence rate of gastric cancer based on their contributions to the recurrence of gastric cancer. The beneficial effects of the present disclosure are mainly reflected in: predicting a risk of near-term recurrence after surgery using a predictive model, which has a great significance for clinical practice and individualized selection of treatment plans.

As used herein, conditions of "poor prognosis" include possible recurrence, possible death, or both.

Establishment of TAPINTO Algorithm

Identifying tumor-associated antigens (TAAs) overexpressed in a subgroup of tumor patients is a significant challenge for targeted therapy. Although there are several methods based on the concept of differential expression levels, there is a lack of proper algorithms based on the heterogeneous transcriptome expression for exploring effective TAAs. The present disclosure provides an algorithm, TAPINTO, to objectively predict overexpressed TAAs whose expression is heterogeneous in cancer patients. This algorithm exploits the dispersion of expression in a subgroup of patients to create three quantitative parameters (the specific average expression, frequency, and fold-change) for evaluating potential TAAs and has a good performance compared with other approaches.

Formulas of TAPINTO algorithm are as follows:

S is a number of samples sorted according to a highest expression level to a lowest expression level.

$$S = 1,2,3, \ldots ,N \qquad \text{[Formula T1]}$$

$x_i$ is an expression level of a sample i, i=1, 2, 3 . . . , s; $\bar{x}_s$ is an average expression level of samples s.

$$\bar{x}_s = \frac{\sum_{i=1}^{s} x_i}{s} \qquad \text{[Formula T2]}$$

$\bar{y}$ is an average expression level of normal samples.

$$\bar{y} = \frac{\sum_{i=1}^{N} y_i}{N} \qquad \text{[Formula T3]}$$

S(s) is a standard deviation of the samples s.

$$SD(s) = \sqrt{\frac{\sum_{i=1}^{s} (x_i - \bar{x}_s)^2}{s-1}} \qquad \text{[Formula T4]}$$

$\hat{S}$ is a maximum standard deviation SD of s.

$$\hat{S} = \arg\max_{0 \leq s \leq N} SD(s) = \sqrt{\frac{\sum_{i=1}^{s} (x_i - \bar{x}_s)^2}{s-1}} \qquad \text{[Formula T5]}$$

Freq is a frequency of high expression subtypes (outliers) in total tumor samples.

$$Freq = \frac{\hat{s}}{N} \qquad \text{[Formula T6]}$$

AvrExp is an average of the high expression subtypes (outliers) in the total tumor samples.

$$AvrExp = \bar{x}_s = \frac{\sum_{i=1}^{s} x_i}{\hat{s}} \qquad \text{[Formula T7]}$$

Fc is a fold-change between the high expression subtypes (outliers) and the normal samples.

$$FC = \frac{AvrExp}{\bar{y}} \qquad \text{[Formula T8]}$$

TAA score is an integral form of three key factors.

$$\text{TAA score} = AvrExp \times Fc \times \qquad \text{[Formula T9]}$$

The 18 genes with the highest scores of TAPINTO are correlated to the survival and metastasis of gastric cancer patients.

The mRNA data of samples of gastric cancer patients were obtained from two public databases: The Cancer Genome Atlas (TCGA) and Gene Expression Omnibus (GEO) (GSE13861 and GSE62254). In TCGA dataset, the 19,814 genes expression from the 375 gastric adenocarcinoma cancer samples and 36 adjacent normal samples were used. These mRNA expression data from TCGA were fragment per kilobase per million (FPKM) normalized. From GSE13861 (ARCG), 299 expression profile of primary gastric tumors (or gastric in situ) and corresponding clinical information were obtained. From GSE26901 (KUCM), 109 expression profile and clinical information of primary gastric tumors were also downloaded. Both datasets are produced from microarray chip platform.

In some embodiments, a detection method of the expression level of RNA includes: microarray, polymerase chain reaction, or sequencing. The polymerase chain reaction includes, but is not limited to, real-time polymerase chain reaction or digital polymerase chain reaction (digital PCR). The sequencing includes, but is not limited to, next-generation sequencing (NGS), single-molecule real-time sequencing (SMRT), or nanopore sequencing.

Based on TAPINTO, three parameters (average, fold-change, and frequency) were calculated for each gene candidate. To evaluate the potential to be an ideal target by the parameters, we had given each candidate a score from zero to six by the TAPINTO scoring method. There were 358 genes given with five points and 18 genes given with six points (Table 1). These genes with the highest scores might have TAAs potential, which is correlated to the tumor prognosis.

TABLE 1

| Gene Name | Average (FPKM) | Fold | Frequency (%) |
|---|---|---|---|
| ANTXR1 | 62.28 | 5.75 | 11.2 |
| SFRP4 | 72.48 | 25.76 | 27.2 |
| COL6A3 | 102.74 | 5.92 | 17.6 |
| THBS2 | 32.74 | 8.10 | 86.4 |
| THBS4 | 68.69 | 11.53 | 15.2 |
| CYP2W1 | 107.77 | 71.09 | 11.47 |
| OLFM4 | 4572.36 | 20.29 | 13.07 |
| F5 | 36.72 | 19.44 | 12.00 |
| CEACAM6 | 800.81 | 12.47 | 17.87 |
| MMP9 | 74.63 | 11.21 | 12.00 |
| TM4SF1 | 301.00 | 8.54 | 10.4 |
| PODXL2 | 63.57 | 7.82 | 14.93 |
| FCER1G | 216.99 | 6.46 | 12.27 |
| PRSS22 | 44.88 | 6.44 | 10.67 |
| NEU1 | 35.55 | 6.21 | 13.60 |
| KCNE3 | 64.95 | 6.13 | 24.53 |
| UBE2S | 36.64 | 5.48 | 26.13 |
| BCAM | 80.74 | 5.42 | 13.87 |

Figure 1:
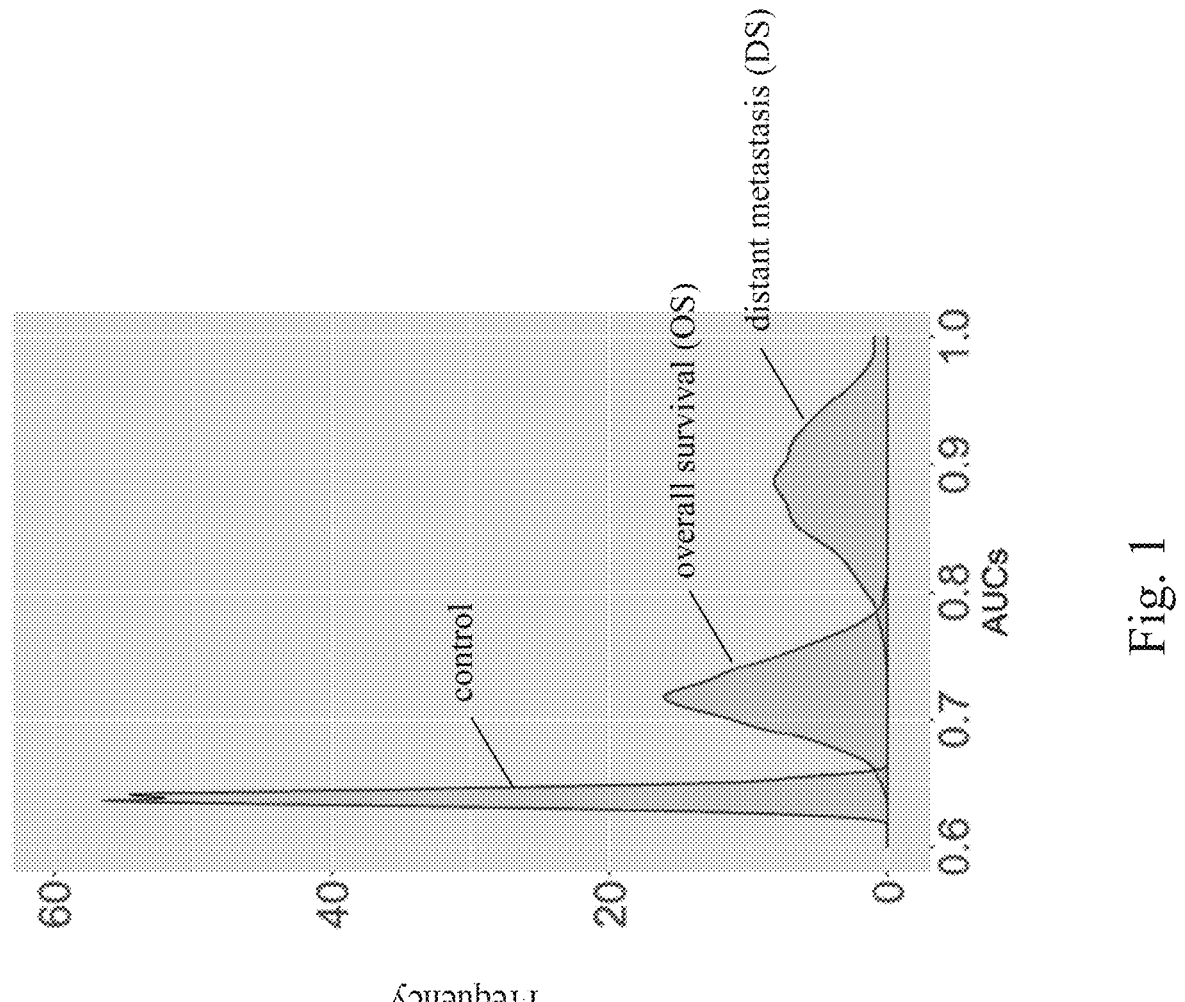
FIG. 1 shows a graph showing area under curve (AUC) of various genes analyzed in different states according to one embodiment of the present disclosure.

To evaluate whether these genes correlated to prognosis (survival and metastasis), we used those gene expressions as variables and the survival/metastasis status as response values to construct the logistic regression for calculating area under curve (AUC) scores. Because the number of samples with survival or metastasis status were not balanced, we processed random sampling for equal numbers between statuses. After training the models, the AUC distributions were evaluated for the accuracy of prognosis prediction by the different sampling of samples. Comprehensively, the distribution of AUCs was calculated from 1,000 times sampling, and the negative control was contrasted by the random setting of tumor samples (FIG. 1).

To process pathway/disease enrichment analysis, we applied the 358 genes with five scores and the 18 genes with six scores for kyoto encyclopedia of genes and genomes (KEGG) pathway and disease gene network (DGN) analysis by R package clusterProfiler. Result shows that gastric cancer-related diseases and KEGG pathways correlated to cancer and signaling pathways were enriched by the gene sets from 376 genes. Tumor angiogenesis and *H. pylori* infection were significantly enriched by the gene sets from 376 genes. Further, the data in FIG. 1 shows that AUC distributions from overall survival (OS) and distant metastasis (DS) were shift to the right of random control, and the DS group had the higher AUCs than the OS group. It demonstrated that these genes are associated with the prognosis, especially metastasis.

Figure 2:
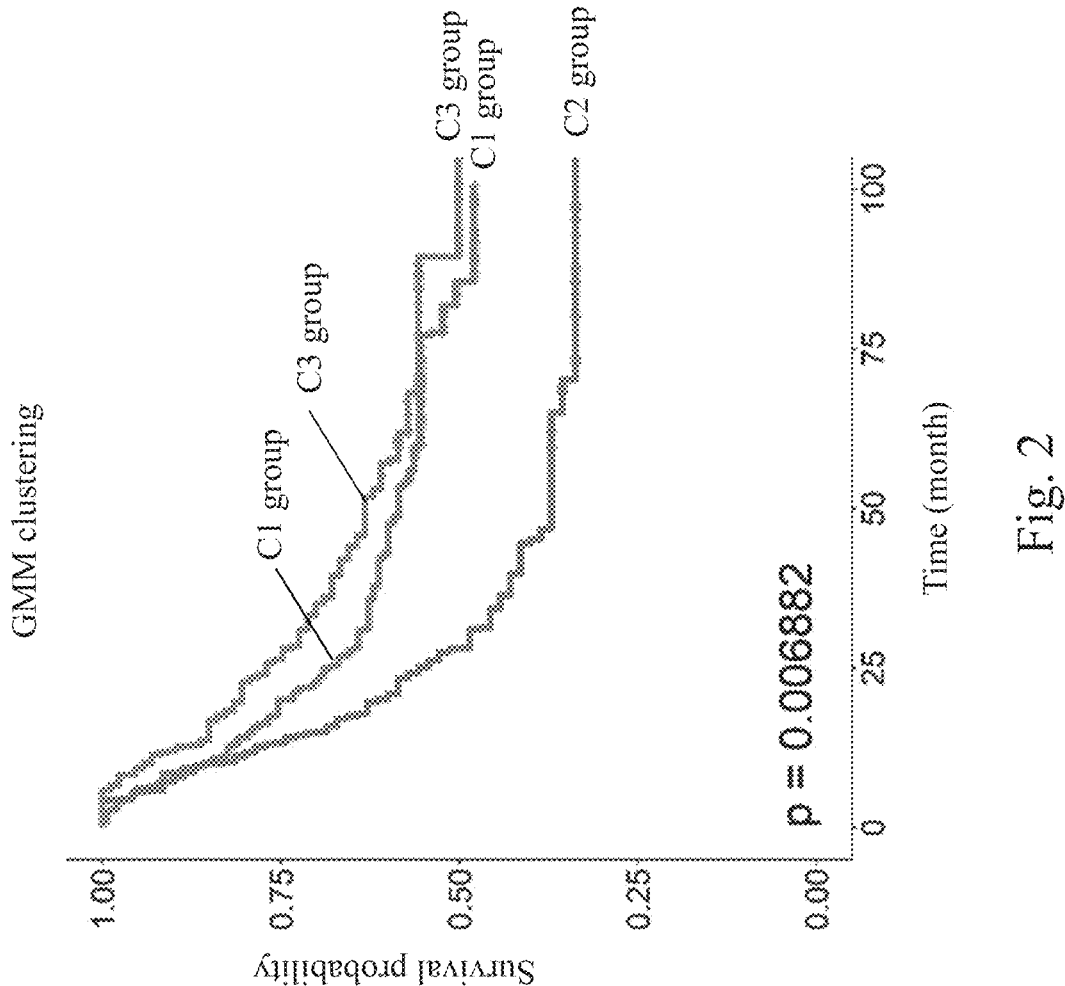
FIG. 2 shows a line chart showing survival probabilities of different groups according to one embodiment of the present disclosure.

To verify whether this association is dependent on a heterogeneous subgroup or whole population, we further evaluated these genes expression for different subgroups and whether correlated to the prognosis and applied another dataset (GSE62254) from GEO. In order to analyze the heterogeneous expression pattern of subgroups, the GC samples were clustered by Gaussian Mixture Model (GMM), a non-supervised clustering method. Finally, the 299 samples could be separated into the three (GSE62254; ACRG) clusters based on the expression of 18 genes, and the overall survival rates were significantly different. As shown in FIG. 2, the ACRG cohort had the significant OS between the three clusters (p-value=0.006882), and the ACRG-C2 group had the poorest OS, and the signature was correlated to the clinical and molecular classification.

High-expressing targets in advanced gastric cancer are associated with poor prognosis.

Figure 3:
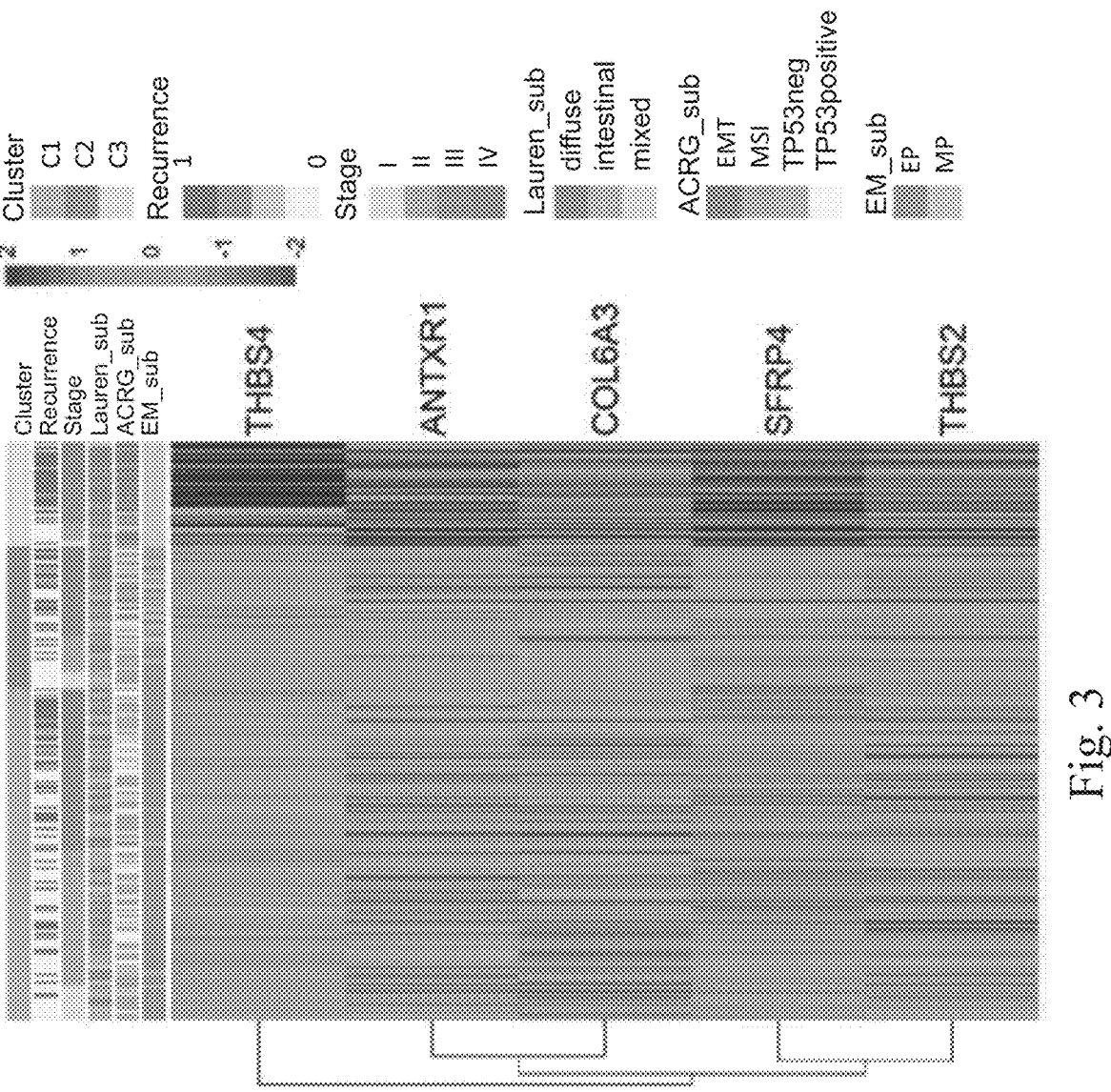
FIG. 3 shows a heat map of an ACRG dataset for five genes according to one embodiment of the present disclosure, in which EMT is epithelial-mesenchymal transition, MSI is microsatellite instability, TP53 is tumor protein p53, EM is epithelioid mesothelioma, EP is epithelial phenotype, and MP is mesenchymal phenotype.
Figure 4:
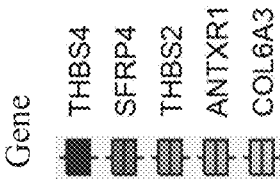
FIG. 4 shows a box plot of expression levels of five genes of different subtypes according to one embodiment of the present disclosure.
Figure 4:
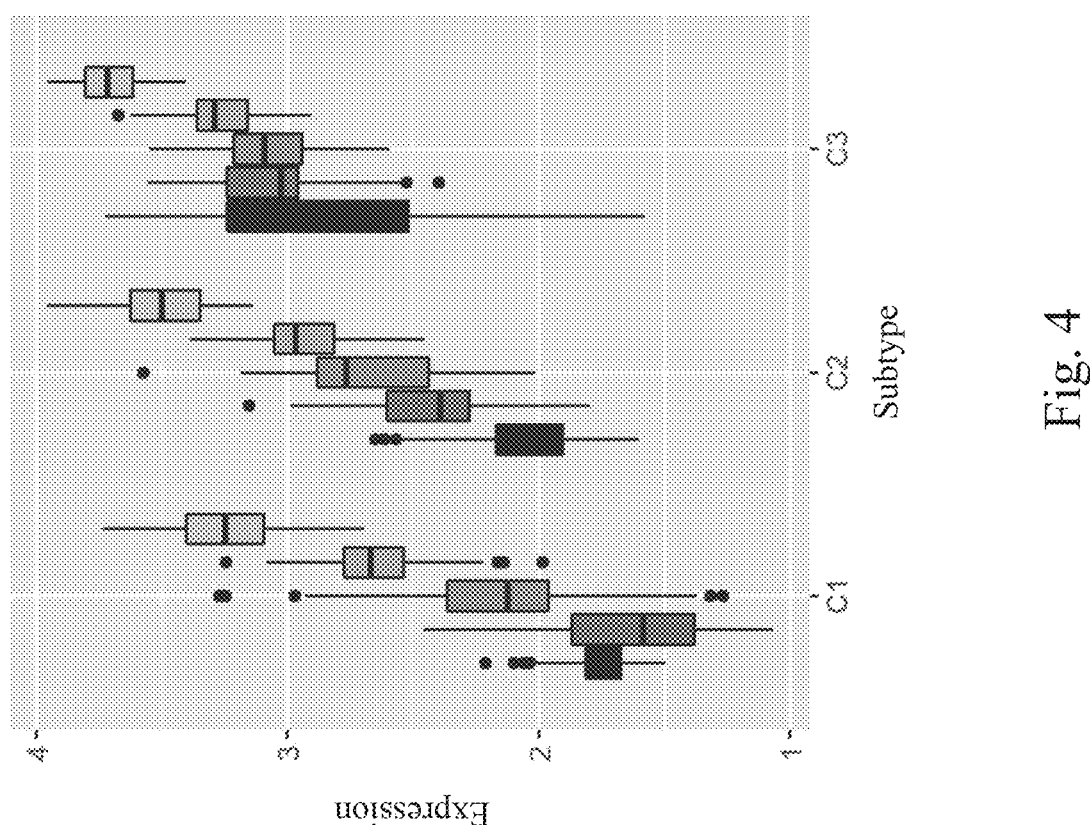
Figure 5:
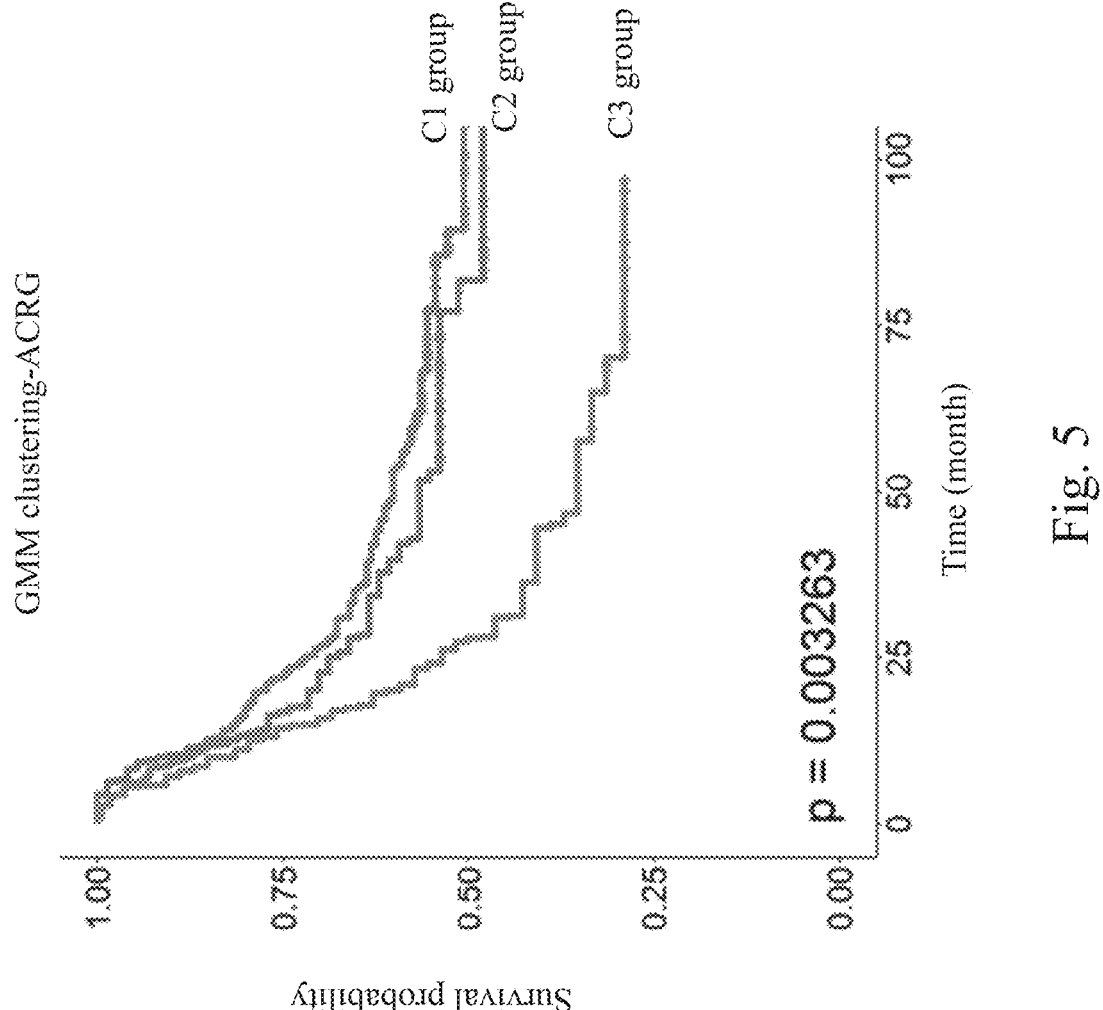
FIG. 5 shows a line chart showing survival probabilities of different groups according to one embodiment of the present disclosure.

In order to evaluate the expression pattern for these different cohorts, a heatmap is presented in the present disclosure. All cohort shows that five genes (ANTXR1, SFRP4, COL6A3, THBS2, and THBS4) were clustered into a gene set by the distance method and specifically overexpressed in a subgroup patient. As shown in FIGS. 3 and 4, the ACRG data set shows that the entire population can be divided into three subtypes (C1, C2 and C3) based on the aforementioned five genes expression levels, of which the C3 group corresponds to more high recurrence rate, diffuse type, epithelial-mesenchymal transition (EMT), and mesenchymal phenotype (MP). See FIG. 5, Kaplan-Meier plot shows the overall survival for GMM clustering based on gene expressions, and the C3 group with highly expressed five genes has the worst overall survival.

Figure 6:
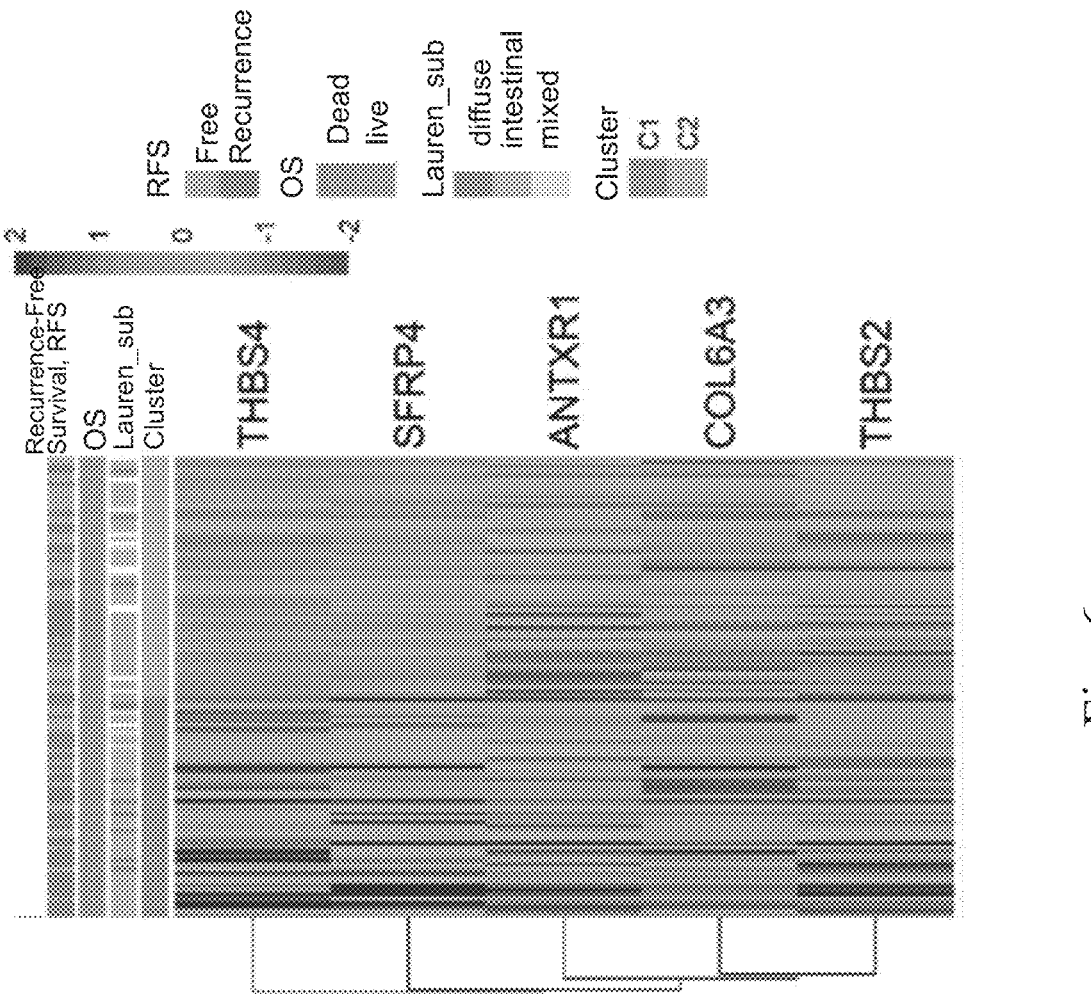
FIG. 6 shows a heat map of a KUCM dataset for five genes according to one embodiment of the present disclosure.
Figure 7:
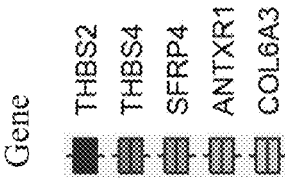
FIG. 7 shows a box plot of expression levels of five genes of different subtypes according to one embodiment of the present disclosure.
Figure 7:
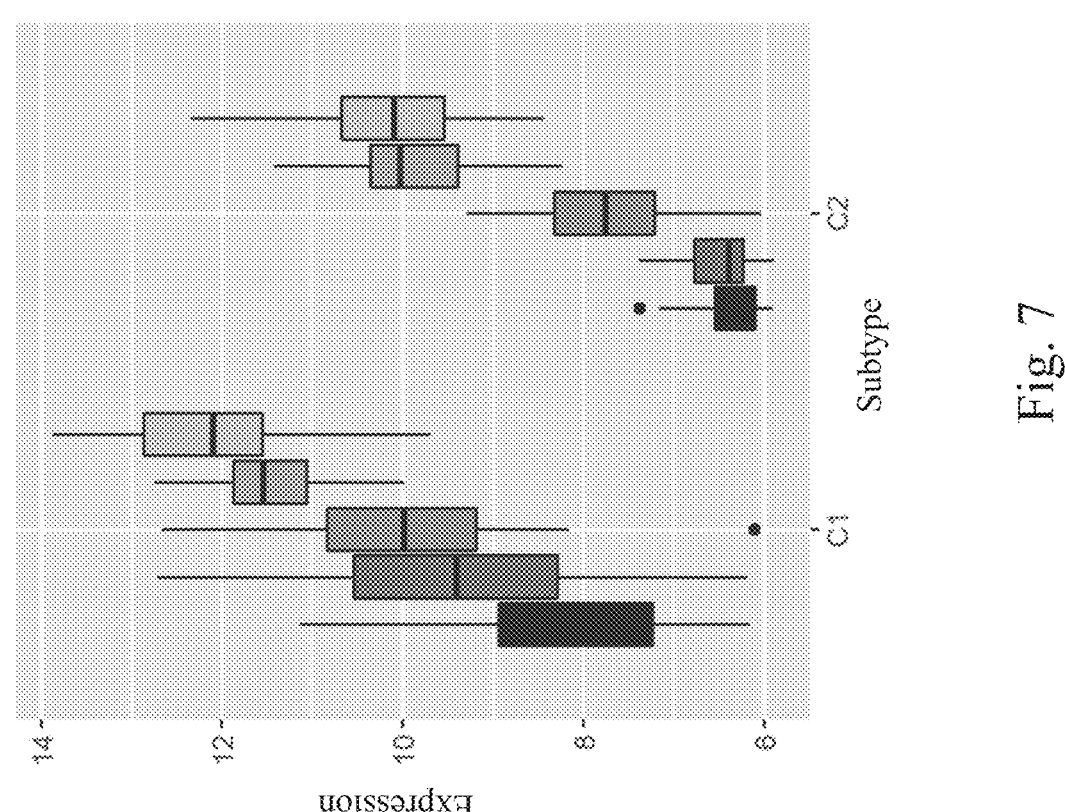
Figure 8:
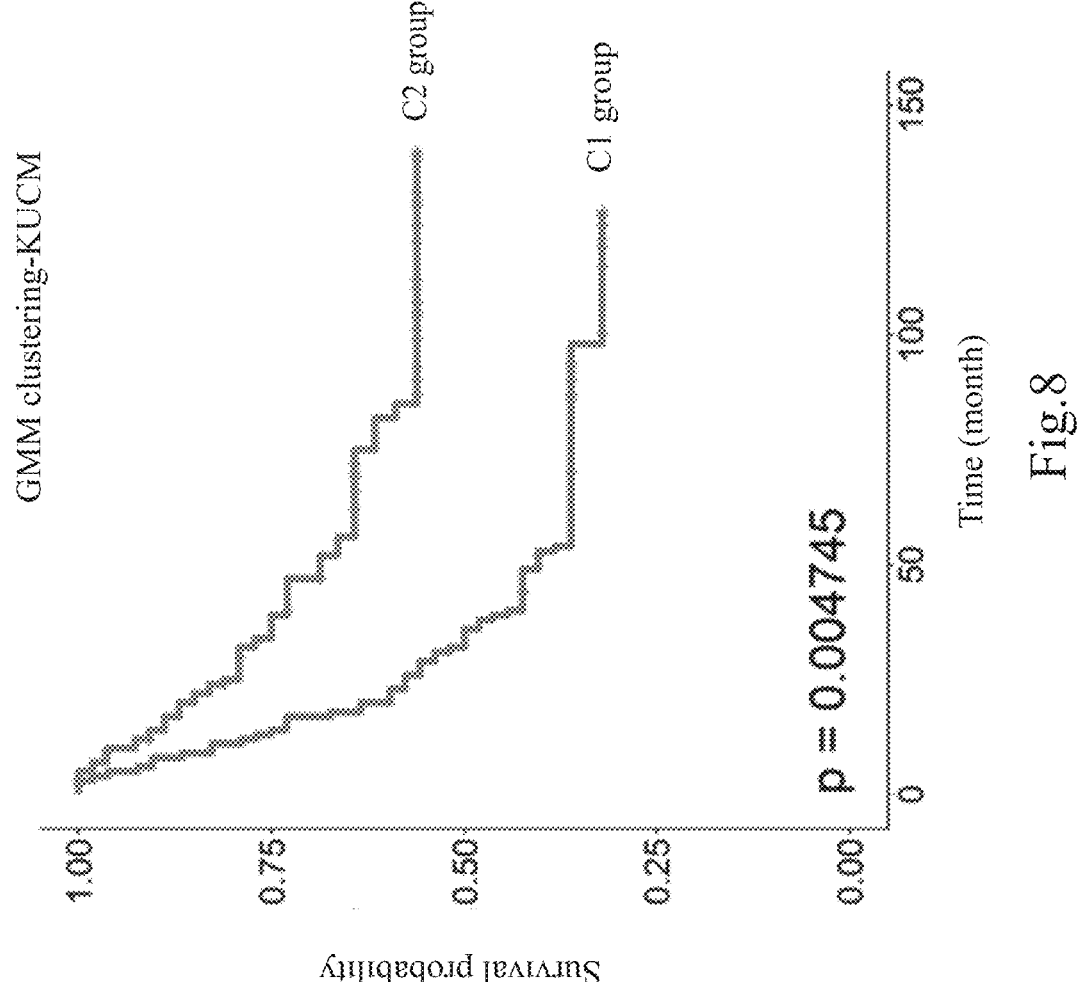
FIG. 8 shows a line chart showing survival probabilities of different groups according to one embodiment of the present disclosure.

The present disclosure uses another dataset, KUCM, to verify the above five genes as the classification of gastric cancer subtypes. As shown in FIGS. 6 and 7, the KUCM dataset shows that the entire population can be divided into two subtypes (C1 group and C2 group) based on the aforementioned five genes expression levels, and the expression levels of the five genes of the C1 group are higher than those of the C2 group, and the C1 group also corresponds to a higher recurrence rate, death, and diffuse type. See FIG. 8, Kaplan-Meier plot shows the overall survival for GMM clustering based on gene expressions, and the C1 group with highly expressed five genes has the worst overall survival.

It demonstrated that this signature might be associated with the OS. In the ACRG cohort, these three subgroups are clustered by the five potential tumor antigens (pTA). Metastasis is often the main cause of recurrence and death, and cancer cells with mesenchymal phenotype have strong metastatic ability. Gastric cancer patients belonging to this type are often more malignant, and a tradition treatment for gastric cancer includes a gastric resection surgery, chemotherapy, radiation therapy, or a combination thereof. Through the prediction of the present disclosure, it will be possible to more closely track the progress of cancer and prepare for drug administration as soon as possible. If the expression levels of the above five genes in the sample are high, it may be mesenchymal phenotype of gastric cancer, and traditional 5FU chemotherapy should not be used. It is recommended to treat with second-line and third-line drugs, such as TGF-β inhibitor, hedgehog inhibitor, PI3K/AKT inhibitor, WNT/β-catenin inhibitor, KRAS inhibitor, etc., and those are used as therapeutic drugs. For example, SB431542, Vismodegib (GDC-0449, Hedgehog inhibitor), Sotorasib (KRAS inhibitor), Linsitinib (high sensitivity to mesenchymal phenotype of gastric cancer), or LY2157299 (Galunisertib, TGF-beta KRAS inhibitor).

A number of examples are provided herein to elaborate the method for predicting a prognosis or recurrence of a gastric cancer patient of the present disclosure. However, the examples are for demonstration purpose alone, and the present disclosure is not limited thereto.

Although a series of operations or steps are used below to describe the method disclosed herein, an order of these operations or steps should not be construed as a limitation to the present disclosure. For example, some operations or steps may be performed in a different order and/or other steps may be performed at the same time. In addition, all shown operations, steps and/or features are not required to be executed to implement an embodiment of the present disclosure. In addition, each operation or step described herein may include a plurality of sub-steps or actions.

Embodiment 1

A combination of genes (ANTXR1, SFRP4, COL6A3, THBS2, and THBS4) was used to predict whether gastric cancer samples were mesenchymal phenotype (MP) prone to metastasis and their risks of recurrence. In the ACRG dataset of 299 in situ gastric cancer samples without any classification, the above five genes were directly used for pattern prediction by the logistic regression. Formula of a risk value Y1 was obtained by applying a linear equation of the logistic regression model to the five RNAs. A relationship between the risk value (dependent variable) and the expression levels of RNAs (independent variables) is expressed by the following equation with fixed coefficients:

$$\text{Risk value } Y1 = 3.9208 * (\text{expression level of ANTXR1 mRNA}) - 0.7496 * (\text{expression level of SFRP4 mRNA}) + 0.8110 * (\text{expression level of THBS2 mRNA}) + 2.6519 * (\text{expression level of THBS4 mRNA}) + 0.9169 * (\text{expression level of COL6A3 mRNA}) - 23.0876 \qquad \text{Equation (1).}$$

The risk value Y1 was transformed with a sigmoid function to obtain a risk ratio Y11.

The expression levels of the above-mentioned five genes were determined by next generation sequencing (NGS), and the expression level values were directly brought in. The risk ratio Y11 was between 0 and 1. The closer the risk ratio Y11 was to 1, the recurrence was present, and 0 was no recurrence. The thresholds were both 0.5. That is, when the expression levels of the five RNAs of each patient were put into Equation (1), and the risk ratio of recurrence calculated by the logistic regression model was greater than or equal to 0.5, it was predicted that the gastric cancer patient had a high probability of belonging to mesenchymal phenotype of the gastric cancer subtype with a high recurrence risk. The equation will vary according to different databases or datasets, but as long as there is a combination of the expression levels of the above five genes, a specific equation with discrimination can be obtained.

Figure 9:
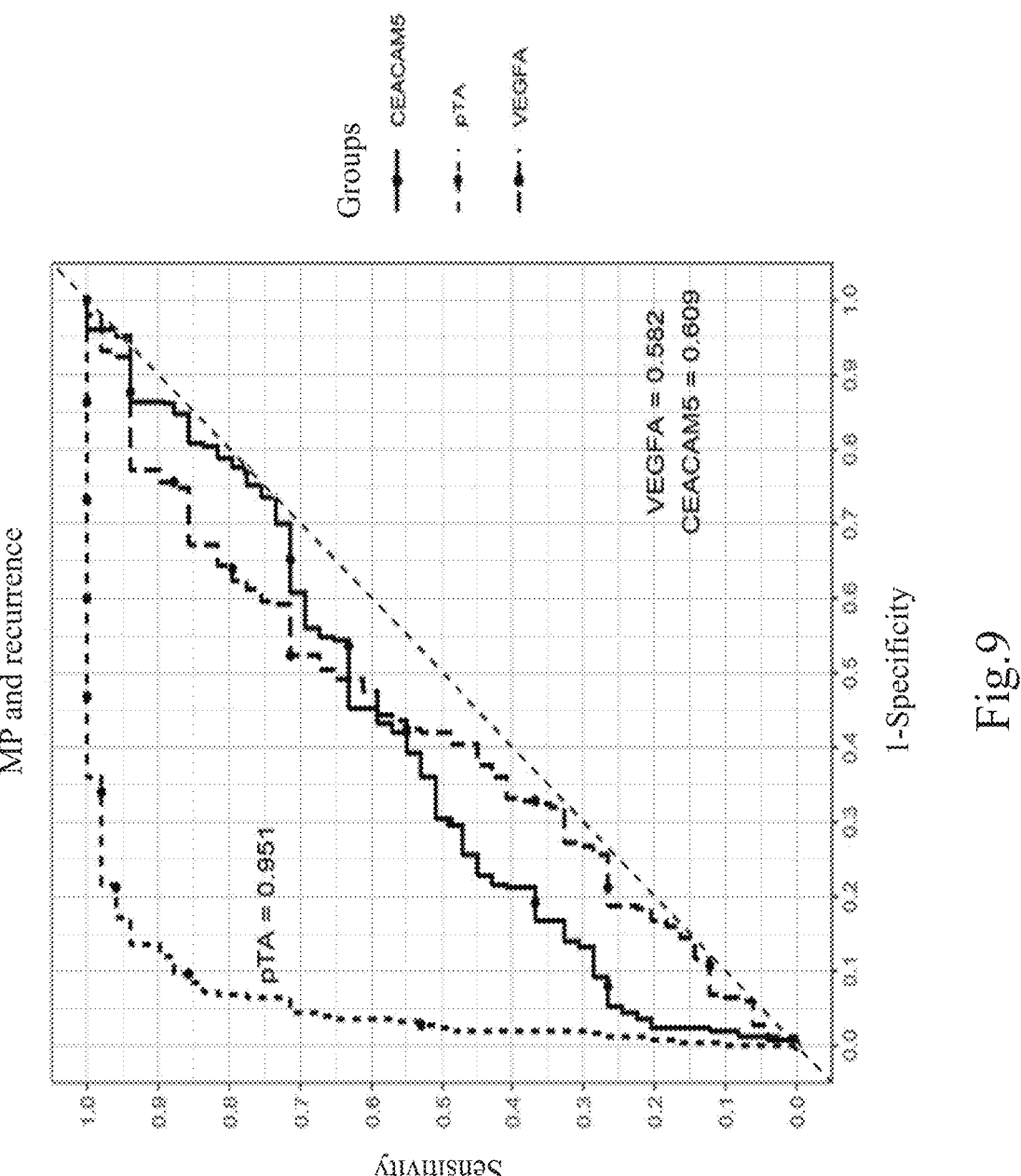
FIG. 9 shows a line chart of AUCs for different genomes with mesenchymal phenotype and recurrence according to one embodiment of the present disclosure.

Next, a receiver operating characteristic curve (ROC curve) was drawn, and an area under the ROC curve (AUC) was calculated, in which AUC=0.65 or less was almost indistinguishable. The larger the AUC value, the better the discrimination ability. See FIG. 9, analysis of mesenchymal phenotype and recurrence shows that the AUC of the five genes (pTA) was as high as 0.951, with excellent discrimination. In contrast, the known target genes VEGFA and CEACAM5 related to gastric cancer had the AUCs of 0.622 and 0.597, respectively, which were almost indistinguishable.

Embodiment 2

The combination of the genes (ANTXR1, SFRP4, COL6A3, THBS2, and THBS4) was used to predict whether the gastric cancer samples were mesenchymal phenotype (MP) prone to metastasis and their risks of death. In the ACRG dataset of 299 in situ gastric cancer samples without any classification, the above five genes were directly used for pattern prediction by the logistic regression. Formula of a risk value Y2 was obtained by applying a linear equation of the logistic regression model to the five RNAs. A relationship between the risk value (dependent variable) and the expression levels of RNAs (independent variables) is expressed by the following equation with fixed coefficients:

$$\text{Risk value } Y2 = 2.9090*(\text{expression level of ANTXR1 mRNA}) - 0.5372*(\text{expression level of SFRP4 mRNA}) - 0.7406*(\text{expression level of THBS2 mRNA}) + 2.4313*(\text{expression level of THBS4 mRNA}) + 2.6100*(\text{expression level of COL6A3 mRNA}) - 24.1446 \quad \text{Equation (2).}$$

The risk value Y2 was transformed with a sigmoid function to obtain a risk ratio Y21.

The expression levels of the above-mentioned five genes were determined by NGS, and the expression level values were directly brought in. The risk ratio Y21 was between 0 and 1. The closer the risk ratio Y21 was to 1, the recurrence was present, and 0 was no recurrence. The thresholds were both 0.5. That is, when the expression levels of the five RNAs of each patient were put into Equation (2), and the calculated risk ratio of recurrence was greater than or equal to 0.5, it was predicted that the gastric cancer patient had a high probability of belonging to mesenchymal phenotype of the gastric cancer subtype with a high recurrence risk.

Figure 10:
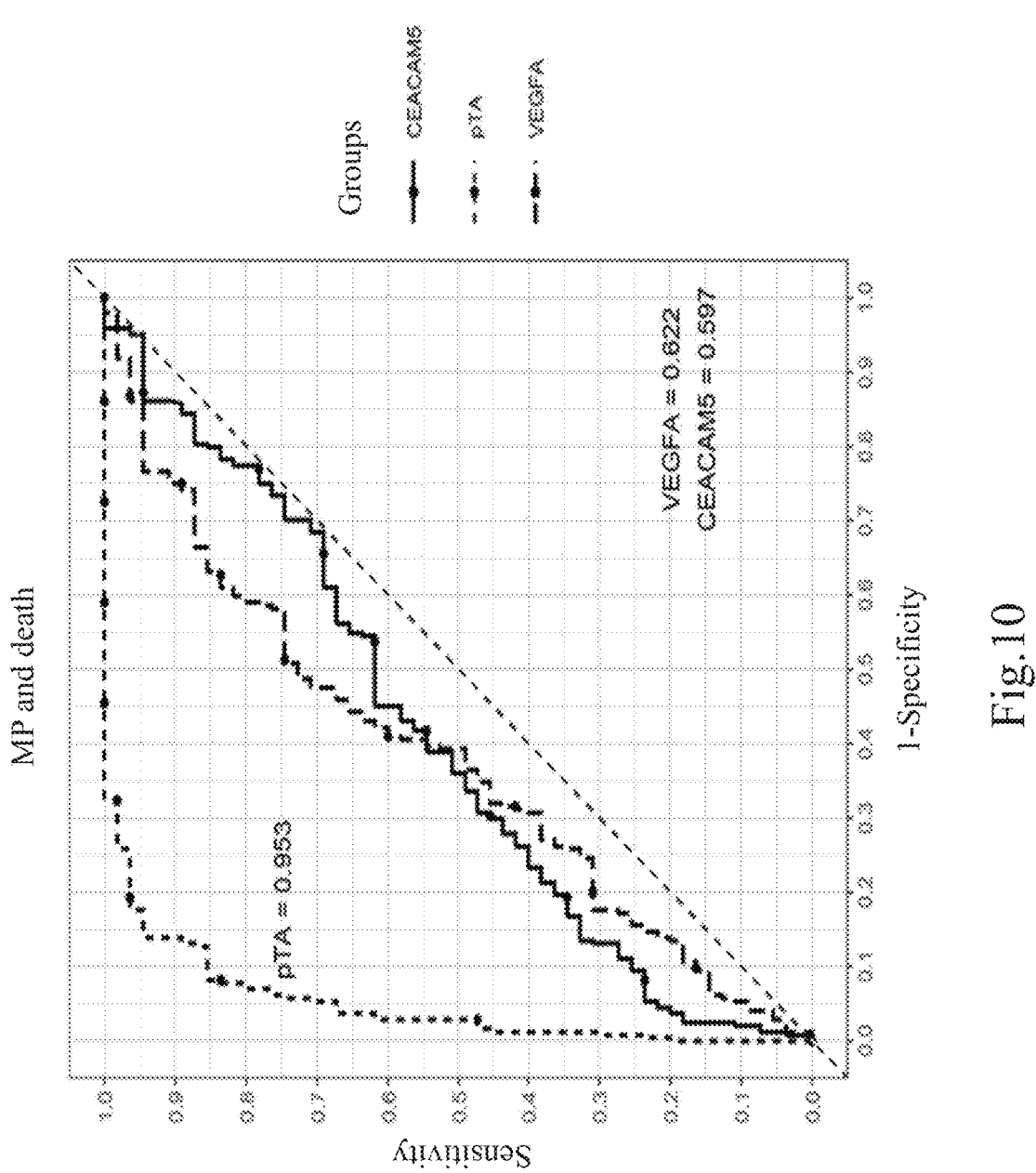
FIG. 10 shows a line chart of AUCs for different genomes with mesenchymal phenotype and death according to one embodiment of the present disclosure.

Next, a ROC curve was drawn, and an AUC was calculated, in which AUC=0.65 or less was almost indistinguishable. The larger the AUC value, the better the discrimination ability. See FIG. 10, analysis of mesenchymal phenotype and death shows that the AUC of the five genes (pTA) was as high as 0.953, with excellent discrimination. In contrast, the known target genes VEGFA and CEACAM5 related to gastric cancer had the AUCs of 0.582 and 0.609, respectively, which were almost indistinguishable.

Embodiment 3

The experimental method was same as that of Embodiment 2. Any one, two, three, four of five of the above five genes were used to predict whether the gastric cancer samples were mesenchymal phenotype prone to metastasis and their risks of death, and pattern prediction was performed by the logistic regression.

TABLE 2

| No. | Genetic combination | AUC |
| --- | --- | --- |
| 1 | ANTXR1 | 0.917 |
| 2 | SFRP4 | 0.912 |
| 3 | COL6A3 | 0.896 |
| 4 | THBS2 | 0.883 |
| 5 | THBS4 | 0.921 |
| 6 | ANTXR1 + SFRP4 | 0.925 |
| 7 | ANTXR1 + COL6A3 | 0.921 |
| 8 | ANTXR1 + THBS2 | 0.918 |
| 9 | ANTXR1 + THBS4 | 0.953 |
| 10 | SFRP4 + COL6A3 | 0.927 |
| 11 | SFRP4 + THBS2 | 0.915 |
| 12 | SFRP4 + THBS4 | 0.942 |
| 13 | COL6A3 + THBS2 | 0.904 |
| 14 | COL6A3 + THBS4 | 0.948 |
| 15 | THBS2 + THBS4 | 0.940 |
| 16 | ANTXR1 + COL6A3 + SFRP4 | 0.928 |
| 17 | ANTXR1 + THBS2 + SFRP4 | 0.925 |
| 18 | ANTXR1 + THBS4 + SFRP4 | 0.953 |
| 19 | ANTXR1 + COL6A3 + THBS2 | 0.920 |
| 20 | ANTXR1 + COL6A3 + THBS4 | 0.952 |
| 21 | ANTXR1 + THBS2 + THBS4 | 0.953 |
| 22 | SFRP4 + COL6A3 + THBS2 | 0.930 |
| 23 | SFRP4 + COL6A3 + THBS4 | 0.950 |
| 24 | SFRP4 + THBS2 + THBS4 | 0.944 |
| 25 | COL6A3 + THBS2 + THBS4 | 0.948 |
| 26 | ANTXR1 + COL6A3 + THBS2 + SFRP4 | 0.931 |
| 27 | ANTXR1 + COL6A3 + THBS4 + SFRP4 | 0.952 |
| 28 | ANTXR1 + THBS2 + THBS4 + SFRP4 | 0.953 |
| 29 | ANTXR1 + COL6A3 + THBS2 + THBS4 | 0.952 |
| 30 | COL6A3 + THBS2 + THBS4 + SFRP4 | 0.951 |
| 31 | ANTXR1 + COL6A3 + THBS2 + THBS4 + SFRP4 | 0.953 |

The results are listed in Table 2. When more genes were included, the AUC was roughly larger, that is, there was a higher prediction rate for predicting whether the gastric cancer samples were mesenchymal phenotype prone to metastasis and their risks of death.

Embodiment 4

The potential tumor antigens (pTAs) expression and signaling pathways were validated in vitro. To validate the association of pTAs with the EMT-like subtype of gastric cancer, the pTAs expression at intestinal-type and diffuse-type GC cell lines were investigated by western blotting. The human GC cell line AGS was obtained from American Type Culture Collection (ATCC) CRL-1739™, and Hs746T was obtained from ATCC HTB-135™, and SNU-1 was obtained from ATCC CRL5971™. Hs746T and SNU-1 were diffuse-type GC cell lines; AGS was an intestinal type GC cell line.

Please refer to FIGS. 11 to 14, ANTXR1, THBS2, THBS4, and SFRP4 were highly expressed by Hs746T or SNU-1 rather than AGS. Thus, high expression in diffuse-type GC cell lines demonstrated that these pTAs might contribute for the malignant characterizations of diffuse-type GC.

Next, significant activation of TGF-β, hedgehog, PI3K, WNT/β-catenin and KRAS signaling pathways were significantly enriched in EMT-like subtype of gastric cancer by gene sets enrichment analysis (GSEA) (data not shown). Therefore, two inhibitors (SB431542 and GDC-0449 (Vismodegib)) were used to validate whether the TGF-β and hedgehog signaling pathways were activated in diffuse-type GC cell lines, respectively. The experiments were performed in triplicate.

Please refer to FIG. 15. The results show that cell viabilities of the two diffuse-type GC cell lines Hs746T and SNU-1 were significantly decreased after the use of 2.5 μM, 5 μM and 10 μM of the TGF-8 inhibitor SB431542, indicating that it had effects of inhibiting the diffuse-type GC cells; however, it did not have significant effects of inhibiting the intestinal type GC cell line AGS. Please refer to FIG. 16, the results show that cell viabilities of the two diffuse-type GC cell lines Hs746T and SNU-1 were significantly decreased after the use of 2.5 μM, 5 μM and 10 μM of the hedgehog inhibitor GDC-0449, indicating that it had effects of inhibiting the diffuse-type GC cells; however, it did not have significant effects of inhibiting the intestinal type GC cell line AGS, and it even had effects of promoting proliferation at the concentrations of 2.5 μM and 5 μM.

Embodiment 5

The kit of the present disclosure may be in a form of a test kit. The kit includes common reagents for PCR reactions, such as primers or probes for RNA detection, buffer, deoxyribonucleotide triphosphate (dNTP), magnesium chloride, pure water, and Taq polymerase. The primers or probes for detecting RNA are designed for the genes of ANTXR1, SFRP4, COL6A3, THBS2, and THBS4, and are designed through known primer or probe design websites. In some embodiments, the probes or primers therein may be immobilized on a solid support, such as a wafer. Next, microarray, polymerase chain reaction, or sequencing is performed to obtain the expression levels of the five RNAs. Finally, at least one of the following two assessments is performed.

1. The expression levels of the five RNAs in a control are compared with the expression levels of the five RNAs in a sample, when the expression levels of the five RNAs in the sample are lower than the expression levels of the five RNAs in the control, the gastric cancer patient is identified as having a poor prognosis, possible recurrence, or possible death.

2. The procedure as in Embodiment 1 and Embodiment 2 is performed. When the AUC of the gastric cancer patient is greater than the AUC of the control, the gastric cancer patient is identified as having a poor prognosis, possible recurrence, or possible death.

In some embodiments of the present disclosure, the tumor-specific antigens should meet the following three characteristics and be further quantified into three parameters to evaluate and screen out the tumor-specific antigens that are overexpressed in cancer subtypes:

1. Compared with normal cells, the antigen gene has a higher expression level in cancer cells.

2. Compared with other genes, the antigen gene has a higher expression level in cancer cells.

3. A higher proportion of patients in a specific cancer group are overexpressed in the antigen gene.

Regardless of the mixed Gaussian non-supervised clustering method or the logistic regression supervised classification method, the five genes screened by the disclosed algorithm can effectively identify the group with higher risks of death and recurrence.

The present disclosure proposes that the five genes can be used to predict whether an in situ gastric cancer sample is mesenchymal phenotype and is likely to recur or die. Compared with other current gastric cancer biomarkers, it does have a higher prediction rate.

Although the present disclosure has been disclosed in the above embodiments, it is not intended to limit the present disclosure. Anyone familiar with this technique can make various changes and modifications without departing from the spirit and scope of the present disclosure. The scope of protection of the present disclosure shall be subject to the scope of appended claims.

What is claimed is:

1. A method for predicting a prognosis of a gastric cancer patient and treating the gastric cancer patient, comprising:

measuring expression levels of five ribonucleic acids (RNAs) in a sample of the gastric cancer patient, the five RNAs being ANTXR1, COL6A3, THBS2, THBS4 and SFRP4;

calculating the expression levels of the five RNAs by a logistic regression model to obtain a risk value $Y1=3.9208*(ANTXR1)-0.7496*(SFRP4)+0.8110*(THBS2)+2.6519*(THBS4)+0.9169*(COL6A3)-23.0876$     Equation (1); and transforming the risk value Y1 through a sigmoid function to obtain a risk ratio between 0 and 1, wherein when the risk ratio is greater than 0.5, the gastric cancer patient is identified as a mesenchymal phenotype of a gastric cancer subtype, and the prognosis is poor; and administrating a treatment to the patient who is at risk of the mesenchymal phenotype of the gastric cancer subtype, wherein the treatment is a gastric resection surgery, chemotherapy, radiation therapy, or a combination thereof.

2. The method of claim 1, wherein the sample is ex vivo gastric tissue.

3. The method of claim 1, wherein a measuring method of the expression levels of the five RNAs comprises microarray, polymerase chain reaction, or sequencing.

4. The method of claim 3, wherein the polymerase chain reaction comprises real-time polymerase chain reaction or digital polymerase chain reaction.

5. The method of claim 3, wherein the sequencing comprises next-generation sequencing, single-molecule real-time sequencing, or nanopore sequencing.

6. A method for predicting a prognosis of a gastric cancer patient and treating the gastric cancer patient, comprising:

measuring expression levels of five ribonucleic acids (RNAs) in a sample of the gastric cancer patient, the five RNAs being ANTXR1, COL6A3, THBS2, THBS4 and SFRP4;

calculating the expression levels of the five RNAs by a logistic regression model to obtain a risk value $Y2=2.9090*(ANTXR1)-0.5372*(SFRP4)-0.7406*(THBS2)+2.4313*(THBS4)+2.6100*(COL6A3)-24.1446$     Equation (2); and transforming the risk value Y2 through a sigmoid function to obtain a risk ratio between 0 and 1, wherein when the risk ratio is greater than 0.5, the gastric cancer patient is identified as a mesenchymal phenotype of a gastric cancer subtype, and the prognosis is poor; and administrating a treatment to the patient who is at risk of the mesenchymal phenotype of the gastric cancer subtype, wherein the treatment is a gastric resection surgery, chemotherapy, radiation therapy, or a combination thereof.

7. The method of claim 6, wherein the sample is ex vivo gastric tissue.

8. The method of claim 6, wherein a measuring method of the expression levels of the five RNAs comprises microarray, polymerase chain reaction, or sequencing.

9. The method of claim 8, wherein the polymerase chain reaction comprises real-time polymerase chain reaction or digital polymerase chain reaction.

10. The method of claim 8, wherein the sequencing comprises next-generation sequencing, single-molecule real-time sequencing, or nanopore sequencing.

11. A method for predicting a prognosis of a gastric cancer patient and treating the gastric cancer patient, comprising:

measuring expression levels of five RNAs in a sample of the gastric cancer patient, and the five RNAs being ANTXR1, COL6A3, THBS2, THBS4 and SFRP4;

calculating the expression levels of the five RNAs in the sample of the gastric cancer patient by a receiver operating characteristic curve to obtain an area under curve of the gastric cancer patient;

calculating the expression levels of the five RNAs by a logistic regression model to obtain a risk value $Y1=3.9208*(ANTXR1)-0.7496*(SFRP4)+0.8110*(THBS2)+2.6519*(THBS4)+0.9169*(COL6A3)-23.0876$      Equation (1); and transforming the risk value Y1 through a sigmoid function to obtain a risk ratio between 0 and 1;

evaluating a risk of a poor prognosis of the gastric cancer patient, wherein when the risk ratio is greater than 0.5, the gastric cancer patient is identified as a mesenchymal phenotype of a gastric cancer subtype, and the prognosis is poor; and administrating a treatment to the patient who is at risk of the mesenchymal phenotype of the gastric cancer subtype, wherein the treatment is a gastric resection surgery, chemotherapy, radiation therapy, or a combination thereof.

12. The method of claim 11, wherein the area under curve of the gastric cancer patient is greater than 0.9.

13. The method of claim 11, wherein the sample is ex vivo gastric tissue.

14. The method of claim 11, wherein a measuring method of the expression levels of the five RNAs comprises microarray, polymerase chain reaction, or sequencing.

15. The method of claim 14, wherein the polymerase chain reaction comprises real-time polymerase chain reaction or digital polymerase chain reaction.

16. The method of claim 14, wherein the sequencing comprises next-generation sequencing, single-molecule real-time sequencing, or nanopore sequencing.

* * * * *